United States Patent [19]
Nilsson et al.

[11] Patent Number: 5,970,160
[45] Date of Patent: Oct. 19, 1999

[54] EARMUFF

[75] Inventors: Lars Bertil Nilsson, Ängelholm; Per Olof Hiselius, Lund, both of Sweden

[73] Assignee: Dalloz Safety AB, Billesholm, Sweden

[21] Appl. No.: 08/860,712

[22] PCT Filed: Jan. 30, 1996

[86] PCT No.: PCT/SE96/00105

§ 371 Date: Jul. 10, 1997

§ 102(e) Date: Jul. 10, 1997

[87] PCT Pub. No.: WO96/23462

PCT Pub. Date: Aug. 8, 1996

[30]     Foreign Application Priority Data

Feb. 1, 1995 [SE] Sweden ................................. 9500368

[51] Int. Cl.⁶ ................................................. H04R 25/00
[52] U.S. Cl. ........................... 381/371; 381/370; 181/129
[58] Field of Search ..................... 381/370, 372, 381/373, 309, 71.6, 74, 371, FOR 149, 150; 181/129

[56]         References Cited

U.S. PATENT DOCUMENTS

| | | |
|---|---|---|
| 2,672,864 | 3/1954 | Makara ..................... 381/370 |
| 4,856,118 | 8/1989 | Sapiejewski . |
| 4,993,074 | 2/1991 | Caroll . |
| 5,020,163 | 6/1991 | Aileo et al. . |

FOREIGN PATENT DOCUMENTS

| | | | |
|---|---|---|---|
| 2579455 | 3/1985 | France | ................................ 381/370 |
| 450546 | 10/1986 | Sweden | ................................ 181/129 |
| 95003687 | 8/1997 | Sweden | ................................ 381/378 |

*Primary Examiner*—Huyen Le
*Assistant Examiner*—Phylesha Dabney
*Attorney, Agent, or Firm*—Greenblum & Bernstein, P.L.C.

[57]            ABSTRACT

Earmuff and method for changing the noise attenuation characteristic of an earmuff. The change is obtained by providing foam-filled sealing ring of the earmuff in the annular covering thereof with a large number of ventilation apertures which are uniformly distributed along the sealing ring, thereby affecting the air spring action of the sealing ring. The ventilation apertures communicate with the environment without communicating with interior of the earmuff. By reducing the air spring action to a considerable extent, the low frequency attenuation is improved. The communication with the environment provides "acoustic ducts", particular by using special ventilation ducts which can be dimensioned to give a selective noise transmission, dependent on the duct resonance, into the sealing ring, thereby selectively affecting the noise attenuation characteristic.

41 Claims, 5 Drawing Sheets

EARMUFF

FIELD OF THE INVENTION

The present invention relates generally to an earmuff of the type having a cup with an elastic sealing ring arranged along the opening circumference of the cup. The sealing ring includes an annular covering and, arranged therein, elastic material, preferably foam material. More specifically, the invention relates to a method for changing the noise attenuation characteristic of such an earmuff, as well as an earmuff obtained in accordance therewith.

BACKGROUND OF THE INVENTION

In most cases, earmuffs of the type mentioned by way of introduction produce a most satisfactory noise attenuation. However, low frequency attenuation is, as a rule, substantially lower than attenuation at higher frequencies, which in certain applications may be disadvantageous. The noise attenuation characteristic is also in most cases quite uneven, which may also be a disadvantage in certain applications.

To achieve satisfactory noise attenuation, it is important that the sealing ring of the earmuff seal efficiently against the user's head. For the purpose of making it possible for the sealing ring to adapt to the user's head while providing excellent comfort properties and maintaining a good noise attenuation capability, the covering of the sealing ring is, as a rule, provided with a small hole or some small holes. The at least one small hole permits pressure compensation as the sealing ring, while being compressed to some extent, is applied to the user's head around an ear. After that, no substantial penetration of noise into the sealing ring takes place.

OBJECTS OF THE INVENTION

The main object of the present invention is to permit a change in the noise attenuation characteristic of an earmuff while using the sealing ring. It is especially an object of the present invention to change the low frequency attenuation and/or to make the noise attenuation characteristic more even.

A further object of the present invention is to indicate how such a change can occur selectively.

SUMMARY OF THE INVENTION

According to the invention, the above-mentioned objects are achieved by a method and an earmuff having the features as defined herein.

The invention is thus based on the knowledge that the noise attenuation characteristic of the earmuff can be affected by manipulation of the effect of the inner air spring of the sealing ring. Such affecting can be achieved by providing the annular covering with ventilation apertures or passages, by means of which the interior of the sealing ring, after application of the earmuff, communicates with the environment without communicating with the interior of the cup. It is a matter of ventilation apertures of a substantially larger total area than the prior-art pressure compensation holes in the sealing ring covering, which are mentioned by way of introduction.

Preferably, the annular covering of the sealing ring is provided with ventilation apertures which are preferably uniformly distributed in the circumferential direction and which can suitably be ventilation holes, although it would be possible to have a different structure of the annular covering in order to provide the desired ventilation apertures.

It has been found convenient to have ventilation apertures or holes, each having an area of at least about 1 $mm^2$, preferably at least about 2 $mm^2$. A total aperture or hole area of at least about 20 $mm^2$ is preferred, more preferably at least about 30 $mm^2$. Especially, an area of more than 100 $mm^2$ can be used, with excellent results. Regarding the distribution along the sealing ring, the ventilation apertures or holes should suitably have an area of at least about 1 $mm^2$ per centimetre of length, preferably at least about 5 $mm^2$ per centimetre of length.

It has been found to be convenient to let the ventilation apertures communicate with the environment through special ventilation ducts, which can advantageously be arranged in the cup and/or annular covering parts. These ducts yield a possibility of protection against penetration of dirt etc. into the sealing ring from the environment, as well as an additional possibility of selectively affecting the noise attenuation characteristic, as will be described in more detail below.

The ventilation apertures are arranged in the annular covering of the sealing ring preferably in a lower or rear annular covering part, by means of which the sealing ring is attached to or abuts against the cup, ventilation ducts advantageously being arranged in the sealing ring connecting parts of the cup and/or in the lower or rear annular covering part, which can, in a manner known per se, be made stronger and stiffer than the remaining annular covering.

According to one aspect of the invention, the ventilation apertures and their communication with the environment are arranged such that, above all at low frequencies, the air can flow substantially unimpededly out of the interior of the sealing ring to the environment and vice versa, the air spring action of the sealing ring being reduced at least to a substantial extent, which results in a pronounced increase of the low frequency noise attenuation, while obtaining a certain reduction of the noise attenuation at higher frequencies.

It is preferred to arrange ventilation apertures such that the attenuation in a frequency range from about 125 Hz to at least about 500 Hz, most advantageously at least to about 1000 Hz, is kept in an interval having a width of about 20 dB at most, especially about 15 dB at most.

According to another aspect of the invention, ventilation apertures and their communication with the environment are arranged such that a selective noise transmission is possible into the sealing ring for the purpose of affecting the noise attenuation characteristic of the earmuff. To this end, use can advantageously be made of special ventilation ducts of the above-mentioned type. Although such ventilation ducts can be designed such that they affect the noise attenuation to a small extent, it is also easy to dimension all or selected ventilation ducts so as to produce a selectively increased noise transmission into the sealing ring in one or more frequency ranges, which results in the noise attenuation characteristic being affected.

Frequency ranges which are of interest for such selective noise transmission are above all those in which the unaffected noise attenuation of the earmuff is high, thereby obtaining a more even noise attenuation characteristic.

The latter aspect of the invention can be regarded as a possibility of providing selective "acoustic ducts" into the sealing ring from the environment. The noise transmission through each acoustic duct and, thus, the effect on the noise attenuation characteristic will be connected to the resonance frequency that applies to the duct at issue, said resonance frequency being determined by a spring-mass system, the spring being determined by an associated air spring inside the sealing ring and the mass being determined by the dimensions of the duct, above all its length and its area. A narrow and high resonance peak results in a narrower influence on the noise attenuation characteristic, while a wide and low resonance peak results in a wider influence on the noise attenuation characteristic. The appearance of the resonance peak can be affected by introducing a suitable acoustic resistance into the duct.

It will be immediately appreciated that in a preferred embodiment of the invention, in which an "acoustic duct" comprises one or more ventilation apertures in combination with a ventilation duct of the above-mentioned type, it is possible, by selecting a suitable number of ventilation ducts of suitable dimensions and just the right amount of resistance, combined with suitably designed ventilation apertures, to control in an efficient manner the noise attenuation characteristic of the earmuff.

It will also be appreciated that the above-mentioned two aspects of the invention can be combined on one and the same earmuff in a suitable manner.

The invention will now be described in more detail by means of an embodiment with reference to the accompanying drawings.

DESCRIPTION OF THE PREFERRED EMBODIMENTS

Figure 1:
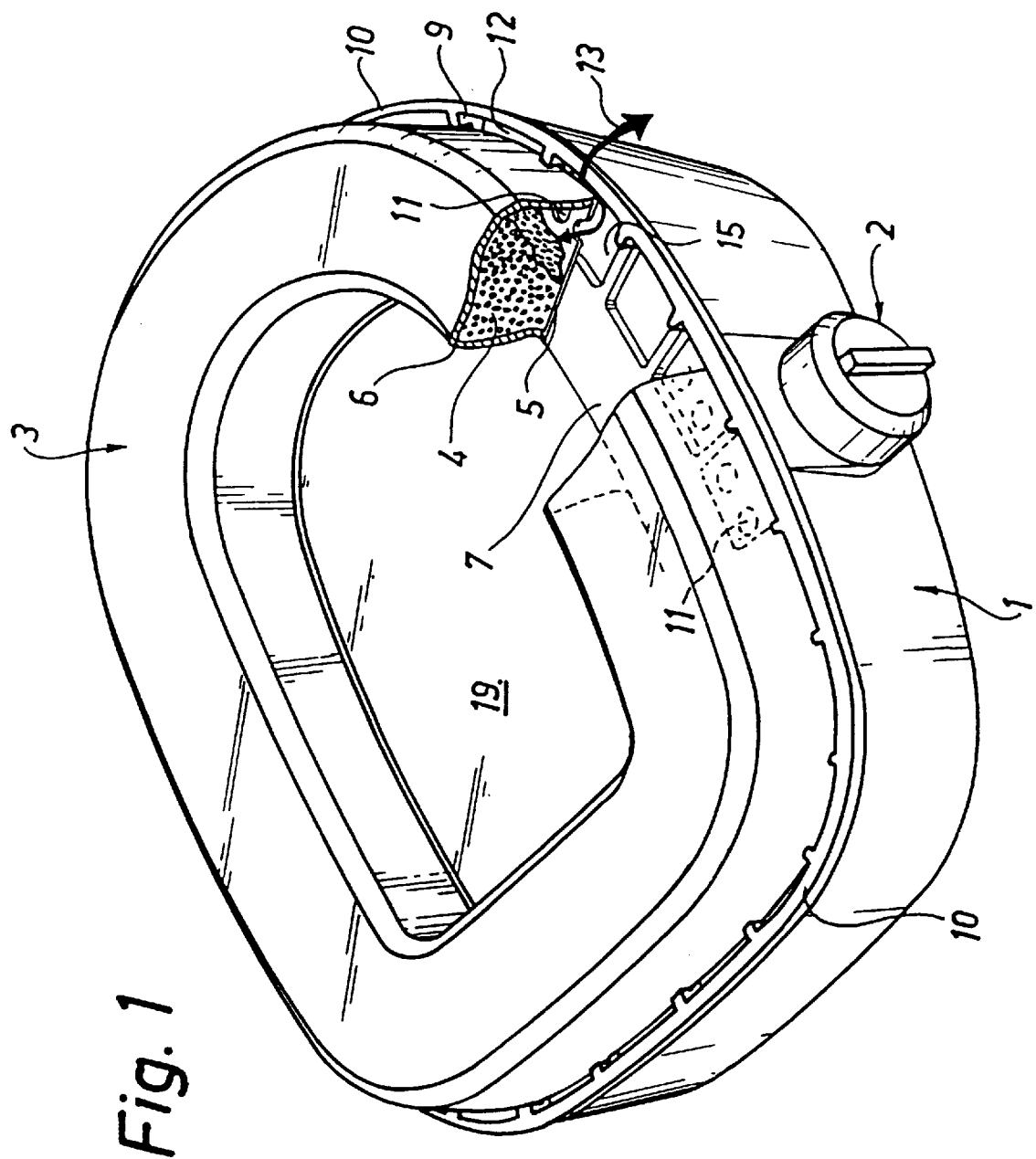
FIG. 1 is a schematic perspective view of a first embodiment of an earmuff according to the invention, part of the sealing ring of the earmuff being cut away for the purpose of illustrating the possibility of air flow between the interior of the sealing ring and the environment.
Figure 2:
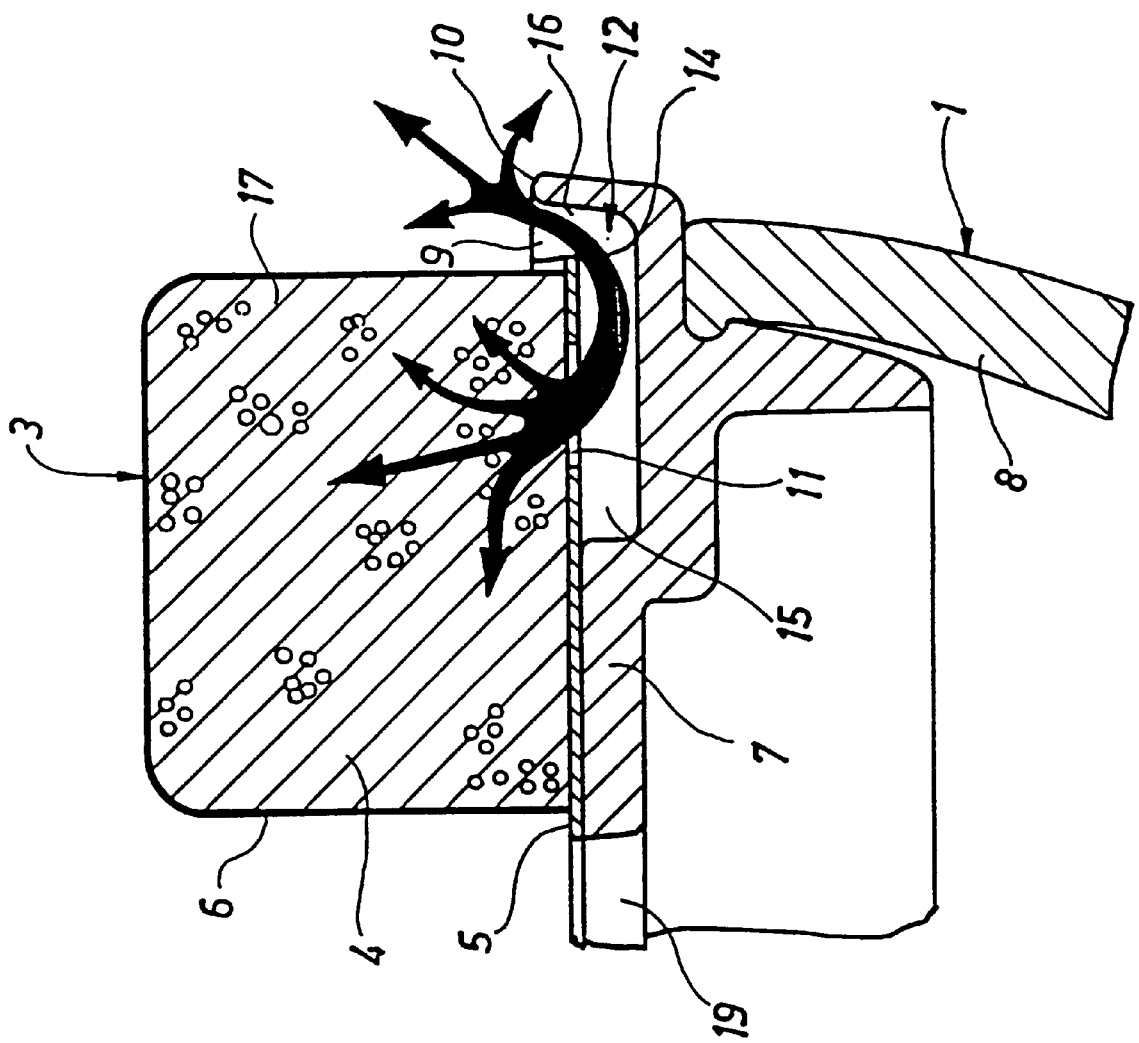
FIG. 2 is a schematic cross-sectional partial view of the sealing ring and connecting cup portions of the earmuff in FIG. 1.

FIGS. 1 and 2 illustrate a first embodiment of an earmuff according to the invention. The earmuff comprises in a known manner a cup 1 having a headband mounting 2 and a sealing ring 3 arranged around the rim area of the cup. The sealing ring 3 comprises an annular covering 5, 6 and, enclosed therein, foam material 4 of an open-cell structure. The foam is of a polyester type and typically has a density of about 25 kg/m$^3$. The annular covering has a stiffer lower or rear part (bottom) 5 in the form of an annular plate and, connected therewith, outwardly directed elastic covering parts 6. The sealing ring 3 is arranged on a planar annular flange 7, which is attached to the cup shell 8 and extends inwardly from the circumference of the cup 1 and, thus, defines an opening 19 to the interior of the cup 1. The sealing ring 3 can be snapped on in the position shown, the outer annular edge of the bottom plate 5 engaging with preferably slightly undercut projections 9 on the circumferential rim 10 of the cup, where the annular flange 7 passes into the rim 10. The projections 9 are distributed around the cup 1.

In the bottom plate 5 of the annular covering 5, 6, a large number of holes 11 are uniformly distributed along the outer edge area of the bottom plate. In FIG. 1, only a few holes 11 are illustrated for the purpose of elucidation. The holes 11 are illustrated as circular, but they could be designed in an optional manner.

For the purpose of providing air flow communication between the holes 11 (and thus the interior of the sealing ring) and the environment, a number of ventilation ducts 12 are arranged in the portions of the cup 1 connecting with the annular covering 5, 6. The ducts 12 are uniformly distributed around the cup, and each duct 12 is, in the embodiment illustrated, adapted to provide air communication with two holes 11 in the bottom plate 5 of the sealing ring. The air flow which is thus made possible is illustrated by arrows 13 and 14 in FIGS. 1 and 2, respectively.

Each duct 12 is formed of a rectangular recess 15 in the upwardly or forwardly facing surface of the annular flange 7 and the space 16 which is formed between the outer circumferential side portion 17 of the annular covering and the rim area 10 of the cup above the connection of the annular flange 7, between two successive projections 9. Thus, the ducts 12 open forwardly, laterally and externally of the sealing ring 3, thereby obtaining satisfactory protection against penetration of, for instance, impurities into the ducts 12. As will be immediately realized, "forwards" here means inwardly in the direction of the user's head, when the earmuff is arranged over an ear. In the embodiment shown, each duct 12 thus is of substantially rectangular cross-section having an essentially constant area. The curved configuration of the ducts 12 means that the length of the duct increases. It will be realised that it is possible to affect in a simple manner the length and the area of the duct by varying the duct configuration in the cup wall and/or the annular flange 7, thereby affecting the noise transmission from the environment into the sealing ring.

The shown design of the ducts 12, which means that the ducts are partially defined by the sealing ring, and that the ducts will be fully open and accessible when the sealing ring is removed, makes it extremely simple to keep the ducts clean. It will also be possible, if desired, to easily change the configuration or dimensions for one or some of the ducts by arranging suitably designed inserts in one or more of the ducts.

A further possibility of easily changing the noise characteristic of an earmuff according to the invention is that the actual sealing ring can readily be exchanged for another sealing ring having a different configuration of the holes in the bottom plate 5.

Figure 4:
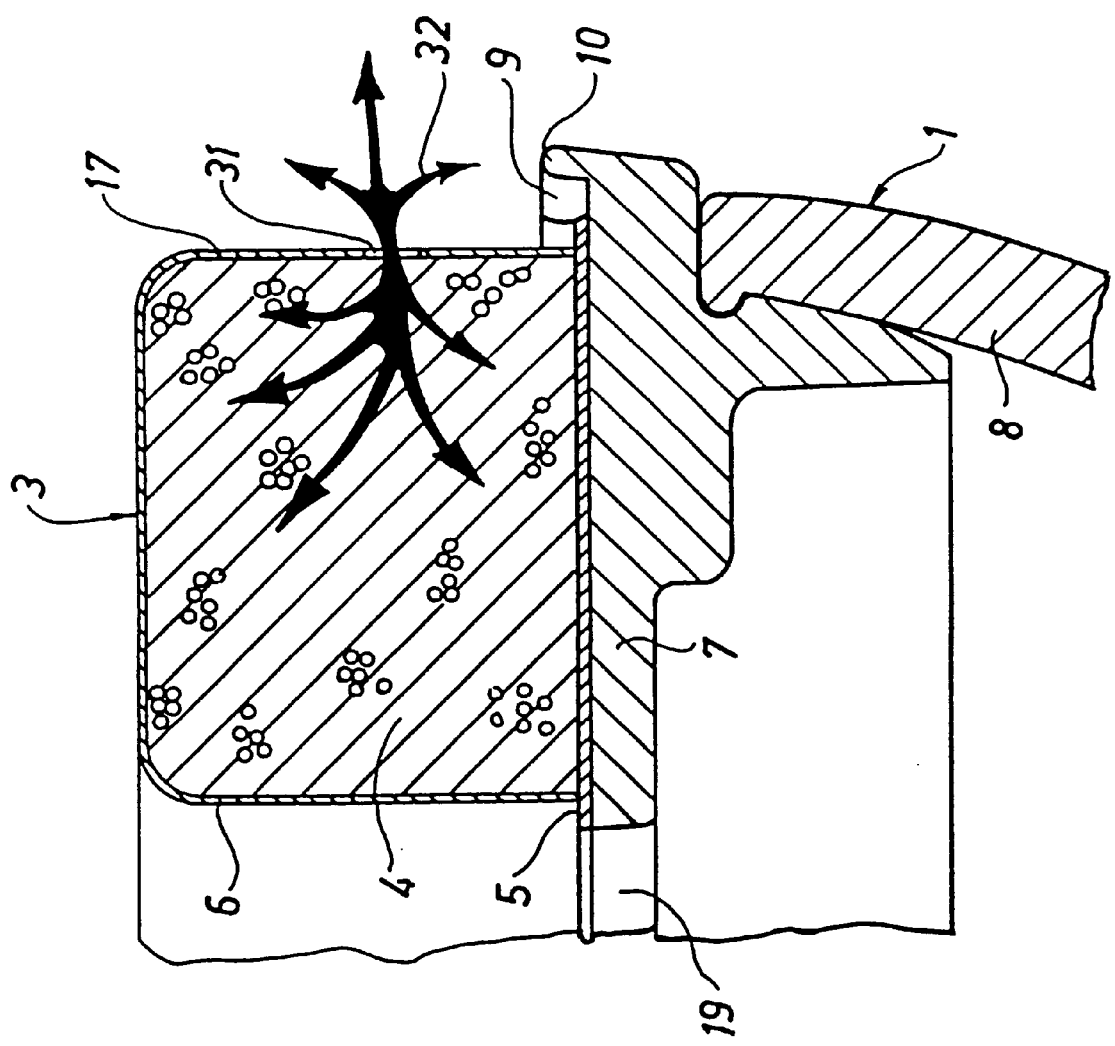
FIG. 4 is a schematic cross-sectional view of the same type as in FIG. 2, but of a sealing ring and connecting cup portions of an earmuff according to a second embodiment of the invention.

FIG. 4 illustrates schematically a second embodiment of an earmuff according to the invention. This differs from the earmuff in FIGS. 1 and 2 merely by ventilation apertures 31 being arranged in the outer circumferential side portion 17 of the annular covering 5, 6. Thus, the bottom plate 5 has no ventilation apertures, and the annular flange 7 has no ventilation ducts.

The ventilation apertures 31 consist of a large number of through holes in the side portion 17 of the annular covering. The holes, which suitably are circular, are uniformly distributed along the sealing ring 3. The holes are here located on the same level in the side portion of the annular covering, more precisely at about half the height thereof. The holes could, however, be positioned on different levels on the ring in a certain pattern for the purpose of ensuring the desired ventilation of the interior of the sealing ring. Like in FIGS. 1 and 2, the air flow into and out of the sealing ring 3 is illustrated by means of arrows 32.

EXAMPLES

Figure 3:
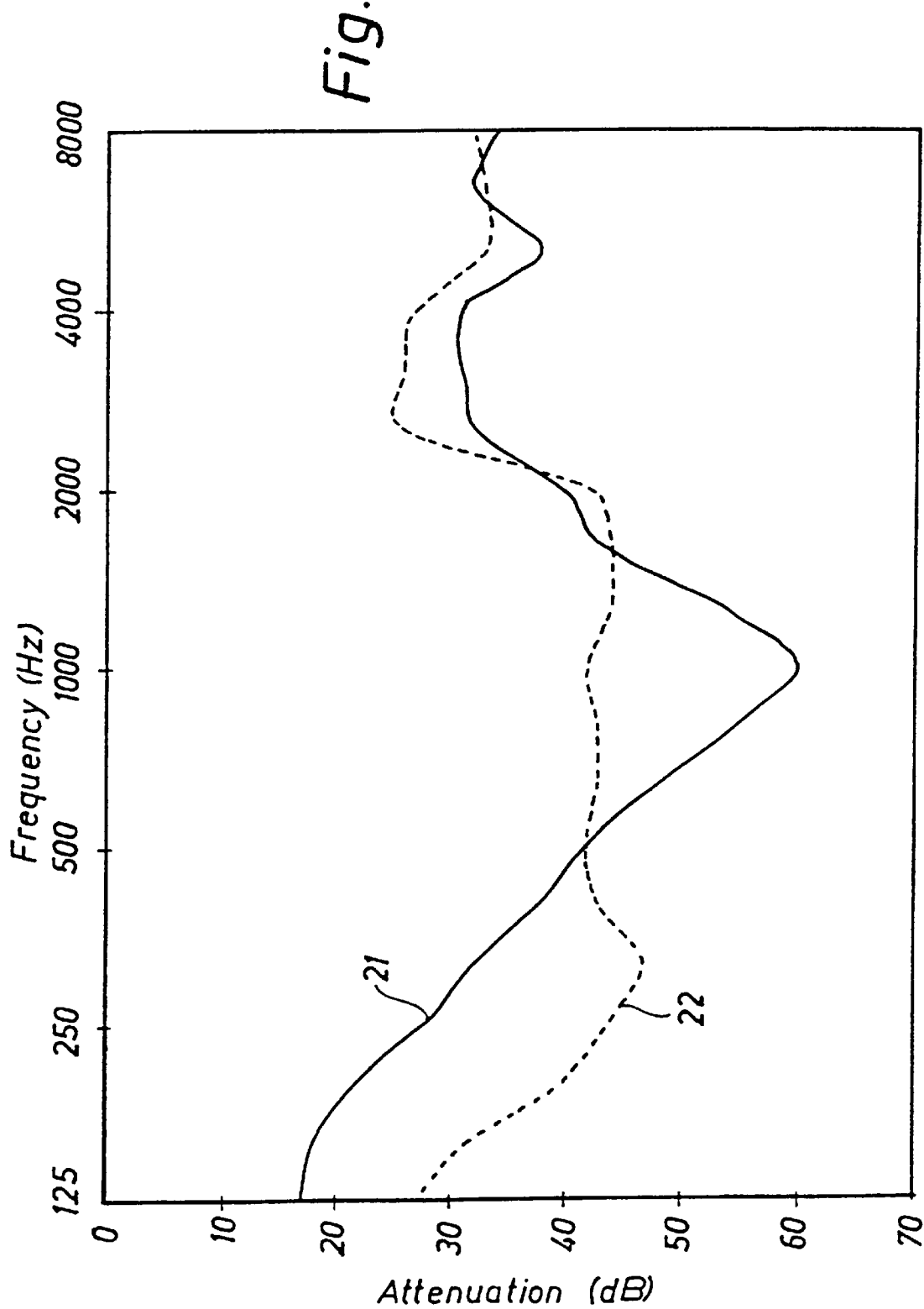
FIG. 3 is a diagram illustrating the noise attenuation characteristic for an ear cup of the type illustrated in FIG. 1, with and without the ventilation arrangement according to the invention.

FIG. 3 illustrates by means of a noise attenuation diagram an example of a change of the noise attenuation characteristic of an earmuff, while using the present invention. The diagram, which shows "insertion attenuation" measured according to ISO 4869-3, indicates by a full line 21 the noise attenuation curve for an earmuff of the type illustrated in FIGS. 1 and 2, although without holes 11 and ducts 12. It is evident that the curve is very uneven, with a low low frequency attenuation and a pronounced attenuation peak at about 1000 Hz.

The diagram also indicates by a dashed line 22 the noise attenuation curve for the earmuff after modification according to the invention. Here the sealing ring has 40 equally large circular holes which are uniformly distributed along the sealing ring, the total area of the holes being about 500 $mm^2$. The number of ducts 12 is 20 and the duct length is about 5–10 mm, and the duct area is about 25 $mm^2$.

As will be seen, a much better low frequency attenuation will be obtained at the expense of a certain reduction of the high frequency attenuation, the attenuation peak of the noise attenuation curve at about 1000 Hz being flattened to a considerable extent. The latter condition indicates that the noise transmission through the ducts 12 into the sealing ring is concentrated to the range around 1000 Hz owing to resonance in this range.

It should be emphasised that changes in the high frequency attenuation that will be a result of the use of the present invention can easily be compensated for or be taken care of, for instance by means of an absorbent arranged in the cup, thereby obtaining the desired total noise attenuation process.

Figure 5:
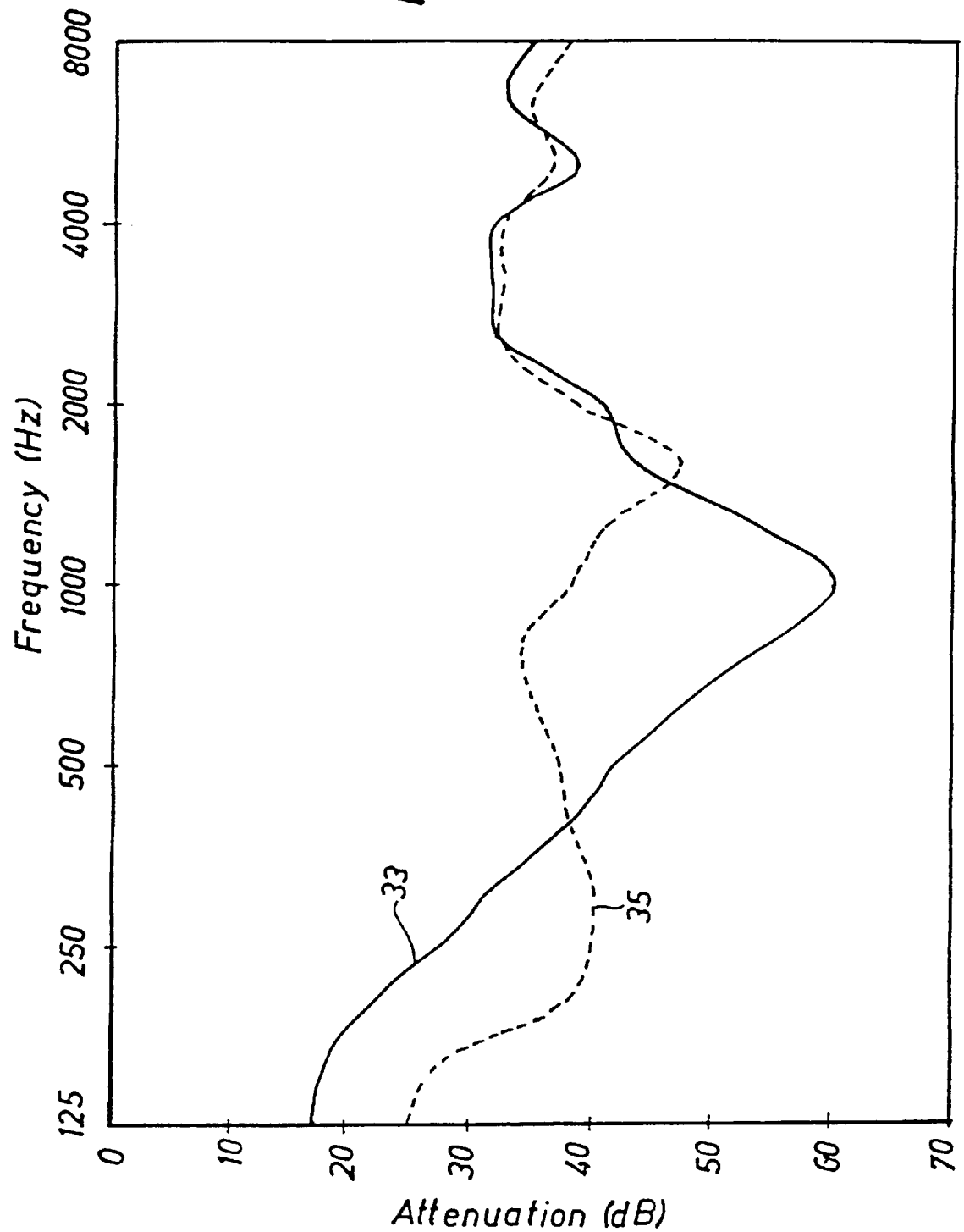
FIG. 5 is a diagram of the same type as in FIG. 3, illustrating the change of the noise attenuation characteristic obtained in the earmuff according to FIG. 4.

FIG. 5 illustrates in the same manner as FIG. 3 the change of the noise attenuation characteristic obtained for an earmuff according to FIG. 4 while using the present invention. The noise attenuation curve for the earmuff before modification according to the invention is indicated by a full line 33. A dashed line 35 indicates the noise attenuation curve after modification, implying that the annular covering 6 of the sealing ring has been provided with 30 equally large and uniformly distributed holes having a total area of about 30 $mm^2$. The thickness of the annular covering 6 ("acoustic duct length") was about 1 mm. As will be seen, a considerably improved evenness of the noise attenuation curve together with an improved low frequency attenuation is achieved.

What is claimed is:

1. An earmuff comprising:
   a cup comprising an interior and an opening including an opening circumference:
   an elastic sealing ring positioned along said opening circumference, said sealing ring including an annular covering forming an interior and an elastic material positioned in said interior;
   ventilation passages associated with said annular covering so that the interior of the sealing ring, after application of the earmuff, communicates with an environment outside said cup, but does not communicate with the interior of said cup; and
   said ventilation passages being distributed circumferentially along said sealing ring and having an area so that air can flow to and from the interior of the sealing ring and the environment to affect air spring action of the sealing ring to a substantial extent.

2. The earmuff according to claim 1, wherein said ventilation passages comprise an area of at least about 1 $mm^2$ per centimeter of length of said sealing ring.

3. The earmuff according to claim 2, wherein said ventilation passages comprise an area of at least about 5 $mm^2$ per centimeter of length of said sealing ring.

4. The earmuff according to claim 1, wherein said ventilation passages are at least substantially uniformly distributed along said sealing ring, and comprise at least an open area so that air can flow substantially unimpededly out of and into said sealing ring to thereby increase noise attenuation at low frequencies.

5. The earmuff according to claim 1, wherein said ventilation passages comprise ventilation apertures uniformly and circumferentially distributed in said annular covering of said sealing ring.

6. The earmuff according to claim 5, wherein each of said ventilation apertures has an area of at least about 1 $mm^2$.

7. The earmuff according to claim 5, wherein each of said ventilation apertures has an area of at least about 2 $mm^2$.

8. The earmuff according to claim 1, wherein said annular covering in an area facing the environment after application of the earmuff is composed of an air-permeable material.

9. The earmuff according to claim 8, wherein said air-permeable material comprises a perforated material or a gauze-like material.

10. The earmuff according to claim 1, wherein said annular covering includes a rear annular covering portion, said ventilation passages being arranged in said rear annular covering portion, and further including ventilation ducts through which said ventilation passages communicate with the environment.

11. The earmuff according to claim 10, wherein said annular covering portion abuts against said cup.

12. The earmuff according to claim 11, wherein said ventilation ducts are arranged in cup portions connecting with the sealing ring.

13. The earmuff according to claim 11, wherein said ventilation ducts are arranged in said rear annular covering portion.

14. The earmuff according to claim 10, wherein said annular covering portion is attached to said cup.

15. The earmuff according to claim 14, wherein said ventilation ducts are arranged in cup portions connecting with the sealing ring.

16. The earmuff according to claim 14, wherein said ventilation ducts are arranged in said rear annular covering portion.

17. The earmuff according to claim 10, wherein said ventilation ducts are distributed around said opening of said cup for ventilation of corresponding portions of said sealing ring.

18. The earmuff according to claim 17, wherein said ventilation ducts communicate with openings in said cup, externally and laterally of said sealing ring.

19. The earmuff according to claim 18, wherein said ventilation ducts include openings facing forward away from said cup.

20. The earmuff according to claim 10, wherein said ventilation ducts are constructed and arranged to produce an increase noise transmission in at least one selected frequency range to thereby effect a total attenuation characteristic of the earmuff.

21. The earmuff according to claim 20, wherein said at least one frequency range is at least one frequency range wherein unaffected noise attenuation of the earmuff is high.

22. The earmuff according to claim 10, wherein the ventilation ducts are curved.

23. The earmuff according to claim 1, wherein said elastic material comprises a foam material having an open-cell structure.

24. The earmuff according to claim 23, wherein said foam material has a density in the range of from about 10 to about 100 kg/m$^3$.

25. The earmuff according to claim 24, wherein said foam material has a density of 25 kg/m$^3$.

26. The earmuff according to claim 23, wherein said foam material comprises a polyester.

27. A method for changing noise attenuation of an earmuff, said earmuff comprising:

a cup comprising an interior and an opening including an opening circumference; and an elastic sealing ring positioned along said opening circumference, said sealing ring including an annular covering forming an interior and an elastic material positioned in said interior; said method comprising:

distributing ventilation passages circumferentially along the annular covering so that the interior of the sealing ring, after application of the earmuff, communicates with an environment outside the cup, but does not communicate with the interior of the cup, to affect air spring action of the sealing ring and the noise attenuation characteristic of the earmuff.

28. The method according to claim 27, comprising selectively affecting the noise attenuation characteristic of the earmuff by at least one of distributing the ventilation passages, changing an opening area of the ventilation passages, and changing an acoustic duct length of the ventilation passages.

29. The method according to claim 27, comprising distributing the ventilation passages at least substantially uniformly over the circumference of said sealing ring, whereby air can flow substantially unimpededly between the interior of the sealing ring and the environment, thereby reducing the air spring action of the sealing ring at least to a substantial extent and increasing the noise attenuation at low frequencies.

30. The method according to claim 27, comprising arranging the ventilation passages as ventilation apertures in the annular covering.

31. The method according to claim 30, comprising uniformly distributing the ventilation apertures along the sealing ring.

32. The method according to claim 31, wherein the ventilation apertures have a total area of at least about 30 mm$^2$.

33. The method according to claim 32, wherein the ventilation apertures have a total area of at least about 100 mm$^2$.

34. The method according to claim 27, comprising arranging the ventilation passages so that the noise attenuation within a frequency range from about 125 Hz to about 500 Hz is kept in an interval having a width of at most about 20 dB.

35. The method according to claim 34, wherein the interval has a width of at most about 15 dB.

36. The method according to claim 27, comprising arranging the ventilation passages so that the noise attenuation within a frequency range from about 125 Hz to about 1000 Hz is kept in an interval having a width of at most about 20 dB.

37. The method according to claim 36, wherein the interval has a width of at most about 15 dB.

38. The method according to claim 27, comprising providing said ventilation passages as ventilation ducts.

39. The method according to claim 38, comprising providing said ventilation ducts so as to produce an increase noise transmission into the sealing ring in at least one frequency range, in which the unaffected noise attenuation of the earmuff is high to thereby obtain a more even noise attenuation characteristic.

40. The method according to claim 38, comprising providing the ventilation ducts and openings of the ventilation ducts so as to produce a noise transmission resonance peak in a selected frequency range.

41. The method according to claim 40, wherein the selected frequency conforms to an attenuation peak in the noise attenuation characteristic of the unaffected earmuff.

* * * * *